(12) United States Patent
Aldykiewicz, Jr. et al.

(10) Patent No.: US 8,603,241 B2
(45) Date of Patent: Dec. 10, 2013

(54) INTEGRALLY WATERPROOFED CONCRETE

(75) Inventors: Antonio J. Aldykiewicz, Jr., Lexington, MA (US); Arnon Bentur, Haifa (IL); Neal S. Berke, Chelmsford, MA (US); Chia-Chih Ou, Lexington, MA (US)

(73) Assignee: W. R. Grace & Co.-Conn., Columbia, MD (US)

( * ) Notice: Subject to any disclaimer, the term of this patent is extended or adjusted under 35 U.S.C. 154(b) by 180 days.

(21) Appl. No.: 12/912,125

(22) Filed: Oct. 26, 2010

(65) Prior Publication Data

US 2011/0036273 A1 Feb. 17, 2011

Related U.S. Application Data

(62) Division of application No. 11/576,382, filed as application No. PCT/US2005/034931 on Sep. 28, 2005, now Pat. No. 7,846,251.

(51) Int. Cl.
*C07D 295/18* (2006.01)
*C04B 40/00* (2006.01)

(52) U.S. Cl.
USPC ............ 106/823; 106/819; 106/822; 106/316

(58) Field of Classification Search
USPC .................................. 106/823, 819, 822, 316
See application file for complete search history.

(56) References Cited

U.S. PATENT DOCUMENTS

| | | |
|---|---|---|
| 2,089,196 A | 8/1937 | Ellis |
| 3,008,843 A | 11/1961 | Jolly |
| 3,048,499 A | 8/1962 | Jellinek |
| 3,287,145 A | 11/1966 | Fischer |
| 3,736,600 A | 6/1973 | Drinkwater |
| 3,865,601 A * | 2/1975 | Serafin et al. .................. 106/659 |
| 3,885,985 A | 5/1975 | Serafin et al. |
| 3,955,994 A * | 5/1976 | Hunter et al. .................. 106/727 |
| 4,017,417 A | 4/1977 | Clark et al. |
| 4,126,470 A | 11/1978 | Braun et al. |
| 4,375,987 A | 3/1983 | Lange et al. |
| 4,788,287 A | 11/1988 | Matsuo et al. |
| 4,846,886 A | 7/1989 | Fey et al. |
| 4,919,839 A | 4/1990 | Durbut et al. |
| 5,108,511 A | 4/1992 | Weigand |
| 5,294,256 A | 3/1994 | Weigland et al. |
| 5,393,343 A | 2/1995 | Darwin et al. |
| 5,415,812 A | 5/1995 | Durbut et al. |
| 5,439,608 A | 8/1995 | Kondrats |
| 5,460,648 A | 10/1995 | Walloch et al. |
| 5,527,388 A | 6/1996 | Berke et al. |
| 5,556,460 A | 9/1996 | Berke et al. |
| 5,603,760 A | 2/1997 | Berke et al. |
| 5,618,344 A | 4/1997 | Kerkar et al. |
| 5,634,966 A | 6/1997 | Berke et al. |
| 5,641,352 A | 6/1997 | Jeknavorian et al. |
| 5,679,150 A * | 10/1997 | Kerkar et al. .................. 106/808 |
| 5,728,209 A | 3/1998 | Bury et al. |
| 5,779,788 A | 7/1998 | Berke et al. |
| 5,938,835 A | 8/1999 | Shawl et al. |
| 6,302,955 B1 * | 10/2001 | Kerkar et al. .................. 106/802 |
| 6,358,310 B1 | 3/2002 | Berke et al. |
| 6,398,865 B1 | 6/2002 | Morita et al. |
| 6,454,850 B2 | 9/2002 | Yamashita |
| 6,479,446 B1 | 11/2002 | Sherry et al. |
| 6,761,765 B2 * | 7/2004 | Lu .................................. 106/823 |
| 6,936,579 B2 | 8/2005 | Urban |
| 7,202,200 B1 | 4/2007 | DeLeo et al. |
| 2003/0089281 A1 | 5/2003 | Berke et al. |
| 2003/0106464 A1 | 6/2003 | Yamashita et al. |
| 2004/0127606 A1 | 7/2004 | Goodwin |
| 2004/0149174 A1 | 8/2004 | Farrington et al. |

FOREIGN PATENT DOCUMENTS

| | | |
|---|---|---|
| JP | 2001180995 | 7/2001 |
| JP | 2002012461 | 1/2002 |
| WO | 99/28264 A1 | 6/1999 |

OTHER PUBLICATIONS

Marcantoni, Form PCT/IPEA/409, International Preliminary Examination Report, PCT/US05/34931, Jun. 22, 2007, 6 pages.
Marcantoni, Form PCT/ISA/210, International Search Report, PCT/US05/34931, Feb. 8, 2006, 2 pages.
Marcantoni, Form PCT/ISA/237, Written Opinion of the International Searching Authority, PCT/US05/34931, Feb. 8, 2006, 3 pages.
JP 10036765 (Yamamoto et al.), Feb. 10, 1998, abstract only.
JP 10036765 (Yamamoto et al.) Feb. 10, 1998, machine translation to English.
JP 09296049 (Sasaki et al.), Nov. 18, 1997, abstract only.
JP 09296049 (Sasaki et al.), Nov. 18, 1997, machine translation into English.

* cited by examiner

*Primary Examiner* — James McDonough
(74) *Attorney, Agent, or Firm* — Craig K. Leon

(57) ABSTRACT

An exemplary composition for enhancing water repellency in cementitious material comprises a hydrophobic material solute that is dissolved in a glycol ether solvent. Thus, the composition is provided in the form of a non-aqueous solution or emulsion wherein water is in a noncontinuous phase. The use of such compositions to modify cementitious compositions and the cementitious materials obtained thereby are also described.

10 Claims, No Drawings

INTEGRALLY WATERPROOFED CONCRETE

This application is a divisional based on Ser. No. 11/576,382 filed Jun. 11, 2007, which issued as U.S. Pat. No. 7,846,251.

FIELD OF THE INVENTION

The present invention pertains to additives and admixtures for hydratable cementitious compositions, and more particularly to additives and admixtures for imparting water repellant properties to cementitious compositions.

BACKGROUND OF THE INVENTION

It is known to incorporate water repellant materials into hydratable cementitious materials such as cement pastes, masonry cements, mortars, and concrete to achieve a degree of moisture impermeability. A cementitious composition which is impermeable to water and dampness, ideally, may not require the application of externally applied moisture barriers such as bituminous coatings or waterproofing membrane laminates.

In U.S. Pat. No. 6,761,765 B2 (issued Jul. 13, 2004), Lu disclosed an emulsion admixture for imparting water repellant properties to cements. The admixture comprised a polymer, a surfactant, and hydrophobic material in the form of organic esters of aliphatic carboxylic acid. The polymer was preferably a latex polymer (e.g., styrene butadiene copolymer latex). The surfactant could include any surfactant capable of emulsifying the hydrophobic material, and most preferably was an ethoxylated nonylphenol. Lu theorized that mixing the emulsified hydrophobic material into the cementitious composition would evenly distribute it throughout the cementitious matrix as well as over its surface. This purportedly prevented water from entering and exiting porous cementitious structures such as blocks, pavers, and retaining wall units (See Col. 4, ll. 17-24).

Emulsified hydrophobic materials, however, were long known and used previously. For example, U.S. Pat. Nos. 3,865,601 and 3,885,985 disclosed additives comprising oil-in-water emulsions that contained a water-insoluble, water-repelling acid component (e.g., tall oil, an emulsifier (e.g., a salt of such an acid)) and a setting time retarding agent (e.g., sucrose). As explained in the background of U.S. Pat. No. 5,108,511, this additive was dispersible in water form so that the risk of overdosing could be minimized. Further, the additive was provided in a form that allowed additional optional components, such as air-entraining agents, to be included. An improved emulsion additive, as described in U.S. Pat. No. 4,375,987, further included an emulsion stabilizer (e.g., a glycol). The stabilizer, as is now well known, prevents oil-in-water emulsions from breaking down when exposed to freezing temperatures during shipping or storage. (See e.g., U.S. Pat. No. 5,108,511 at column 2, lines 11-23).

In U.S. Pat. No. 5,108,511, Wiegland observed that oil-in-water emulsions were unusable when they broke down. Even when stabilizers (such as glycol) were used in such aqueous systems, the emulsion could break down due to extreme temperature fluctuation and long term thermal cycling. Thus, for the express purpose of increasing workability, plasticity, and board life in mortar cement, Wiegland proposed an additive that comprised a salt of stearic acid (e.g., calcium stearate, aluminum stearate), a set retarding carbohydrate, an ethylenic glycol selected from mono-, di-, tri-, and tetraethylene glycols, and cellulose ether. The stearic salt was saponified by heating the stearic acid and lime powder.

The use of oil-in-water emulsions and saponified metal salts (e.g., calcium stearate) has been commercialized in the industry for some time. An emulsion-based, water-repellancy enhancer, added during the intergrinding process for making cement from clinker, is commercially available from Grace Construction Products, Cambridge USA, under the tradename HYDROPHOBE®. A calcium stearate suspension, provided in the form of finely ground calcium stearate powder, dispersed in an aqueous carrier, is commercially available from Grace under the tradename DARAPEL®.

To improve upon the prior art water repellency technology, the present inventors propose to avoid the use of aqueous emulsions or aqueous solvents.

SUMMARY OF THE INVENTION

The present invention provides a novel composition for enhancing water repellency in cement, masonry cement, concrete, and other cementitious materials. In many cases, it is hoped that the moisture permeability in such cementitious materials can be lowered to the point at which an externally-applied waterproofing coating or membrane is eliminated, thereby achieving a reduction of materials and labor expense.

Novel compositions of the invention may be combined with a cement or cementitious material such as concrete, either as an additive (e.g., during intergrinding of clinker to produce cement) or admixture (e.g., to finished cement, mortar, or concrete) in a liquid-dispensible form. This favors accurate, controllable, verifiable dosage amounts.

Exemplary compositions of the invention comprise: a solute portion having at least one hydrophobic material operative to enhance water repellency in a cementitious material; and a non-aqueous solvent portion having at least one glycol ether, which is preferably operative to inhibit drying shrinkage in a cementitious material; said solute and solvent being present in said composition in a ratio of 95:5 to 5:95; said solute and solvent portions being mixed uniformly together in the form of a nonaqueous solution or in the form of an emulsion wherein water is present as a non-continuous phase. It is preferred that the hydrophobic material be non-air-entraining and non-saponified.

Because compositions of the invention are not intended to achieve oil-in-water emulsions, but rather are intended to be used in the form of nonaqueous solutions or emulsions wherein water is present only as a non-continuous phase, the use of surfactants can be avoided. Surfactants often entrain too much air when used in mortars and concretes. Although a certain amount of air, when distributed as fine micro-bubbles, can bestow freeze-thaw durability to mortars and concretes, air levels which are too high may lead to passageways by which moisture can penetrate. It is believed that the present invention provides better air level management in cementitious materials without requiring that defoamers be added.

The present invention allows certain conventional hydrophobic materials to be employed for use in modifying cementitious compositions, and these would include materials that are preferably non-air-entraining in nature. This may be accomplished by dissolving the hydrophobic materials directly in a non-aqueous liquid carrier, one that preferably comprises one or more shrinkage reducing admixtures, such as certain glycol ethers, as will be further discussed hereinafter.

This combination of solute and non-aqueous solvent results in a larger temperature stability range, and eliminates the need for heated storage in colder environments. This is a tremendous advantage when compared with prior art water repellant systems that were based on conventional emulsions or aqueous suspensions.

For example, exemplary hydrophobic materials believed to be suitable for use in the present invention include an aliphatic carboxylic acid or salt or ester thereof, a fatty acid or salt or the ester thereof, a natural or synthetic wax, a natural or synthetic oil, a silicone compound, a silane compound, a siloxane compound, a naphthalene compound, a melamine compound, a dicarboxylic acid or the salt thereof, or a mixture of any of the foregoing.

Especially preferred hydrophobic materials (solute) contemplated for use in the invention include fatty acids such as butyl stearate, butyl oleate, or a mixture thereof while preferred glycol ethers (solvent) include di(oxypropylene)glycol-t-butyl ether (DPTB), di(oxypropylene)glycol-n-butyl ether (DPNB), or a mixture thereof. The solvent may additionally include a low molecular glycol such as di(oxypropylene)glycol (DPG), di(oxyethylene)glycol (DIEG), or mixture thereof.

A further detailed description of exemplary solutes (hydrophobic materials) and solvents (such as glycol ethers) is provided hereinafter.

By avoiding the use of a large water portion, the compositions of the invention will realize several advantages. First, manufacturers can avoid the additional step required for making the aqueous emulsion or dispersion as well as the costs of surfactants and stabilizers. Further, the cost of shipping water that constitutes the bulk of the aqueous emulsion or suspension will be decreased. Furthermore, with little or no water content, the compositions of the invention will be less hospitable to bacteria and other microorganisms.

In further exemplary compositions of the invention, one or more comb polymer superplasticizers, such as poly(oxyalkylene) types as known in the art, may be additionally incorporated to lower the water-to-cement ratio and improve workability or fluidity of the cementitious composition. While such superplasticizers may involve a small amount of water, it is nevertheless preferred that compositions of the invention be substantially devoid of water, e.g., less than 35% and more preferably less than 15% by total volume.

The present invention also concerns methods for enhancing water repellency in cementitious materials, and also concerns cementitious materials containing the above-described water repellency enhancing compositions. Other advantages and features of the invention are described hereinafter.

DETAILED DESCRIPTION OF EXEMPLARY EMBODIMENTS

The inventive compositions of the invention, as previously described, are useful as additives or admixtures for modifying cements and cementitious compositions and materials. The present invention thus also pertains to cementitious materials and methods for enhancing water repellency in them.

The terms "cementitious composition" or "cementitious material" as may be used herein, sometimes interchangeably, include and refer to not only to "cements" but also to pastes (or slurries), mortars, and grouts, such as oil well cementing grouts, shotcrete, and concrete compositions comprising a hydraulic cement binder. The terms "paste", "mortar" and "concrete" are terms of art: pastes are mixtures composed of a hydratable (or hydraulic) cement binder (usually, but not exclusively, Portland cement, Masonry cement, Mortar cement, and/or gypsum, and may also include limestone, hydrated lime, pozzolans such as fly ash and/or granulated blast furnace slag, metakaolin, rice hull ash, and silica fume or other materials commonly included in such cements) and water; "mortars" are pastes additionally including fine aggregate (e.g., sand), and "concretes" are mortars additionally including coarse aggregate (e.g., crushed rock or gravel). The cementitious materials described in this invention are formed by mixing required amounts of certain materials, e.g., a hydraulic cement, water, and fine and/or coarse aggregate, as may be required for making a particular cementitious composition.

In addition, the term "cement" may also include and refer to calcium aluminate cement, hydratable alumina, hydratable aluminum oxide, colloidal silica, silicon oxide, magnesia, in addition to Portland cement and pozzolans as just mentioned above.

The water-to-cement (W/C) ratio used in making cast or spray-applied cementitious mixtures is not believed to be critical to achieving optimal water repellency properties, although a suitable W/C ratio could be from about 0.25 to about 0.60. It is desirable to minimize the amount of water needed so as to consolidate, and to avoid deformities in, the structure formed by the cementitious mixture.

When used as admixtures for modifying cement, concrete, or other cementitious material, the compositions of the invention may be combined with hydratable cement binder material before, during, or after addition of water. Alternatively, the inventive compositions can be added as an interground additive during the manufacturing process wherein clinker is transformed into hydratable cement.

Exemplary compositions of the invention may be generally described as non-aqueous solutions having at least one solute and a non-aqueous solvent present in a ratio of 95:5 to 5:95, and, more preferably, 70:30 to 30:70. Preferably, the solute and solvent portions are mixed uniformly together to form a non-emulsion liquid solution. More preferably, the solute may be present in the composition in an amount of 70 to 30 percent based on total dry weight solids in the composition; while the solvent may be present in an amount of 30 to 70 percent based on total weight of the composition.

Exemplary hydrophobic materials contemplated for use in the invention include but are not limited to aliphatic carboxylic acid or salt or ester thereof, a fatty acid or salt or the ester thereof, a natural or synthetic wax, a natural or synthetic oil, a silicone compound (silane, siloxane), a naphthalene compound, a melamine compound, a dicarboxylic acid or the salt thereof, or a mixture thereof. The most preferred hydrophobic materials which are by themselves non-air-entraining when incorporated into hydratable cementitious compositions. Where the hydrophobic material is incorporated into the solvent in solid form, it is preferable to ground the material as finely as possible to facilitate dissolving of the solute into the solution.

Among the preferred hydrophobic materials, therefore, are aliphatic carboxylic acids, salts, or esters thereof, and in particular the organic (e.g., aliphatic) esters of these carboxylic acids or salts. Preferably, the organic ester of an aliphatic carboxylic acid is represented by the general formula $R_1$-$R_2$, wherein $R_1$ is $C_{12}$-$C_{18}$ aliphatic carboxylic acid ester, and $R_2$ is a linear or branched $C_1$-$C_{10}$ alkyl. Preferred aliphatic carboxylic acid esters include, but are not limited to, stearate, oleate, naturally occurring oils (e.g., coconut oil, castor oil, tall oil fatty acid), laurate, palmitate, myristic ester, linoleic ester, and salts and/or mixtures thereof.

Preferred hydrophobic materials include, but are not limited to, alkyl stearate esters, alkyl oleate esters, and mixtures thereof. Preferably, the organic ester of a stearate has the general formula $C_{17}H_{35}COOR_3$ and the organic ester of an oleate has the general formula $CH_3(CH_2)_7=(CH_2)_7COOR_4$, wherein $R_3$ and $R_4$ are each independently a linear or branched $C_1$ to $C_{10}$ alkyl. A preferred stearate is butyl stearate, and a preferred oleate is butyl oleate. In particularly preferred non-air-entraining hydrophobic materials, both butyl oleate and butyl stearate are used together.

More generally speaking, exemplary compositions of the invention comprise at least one hydrophobic material such as a stearate, an oleate, a laurate, a palmitate, a myristic ester, a linoleic ester, a coconut oil, a castor oil, tall oil fatty acid, or a salt thereof, or a mixture thereof. Preferably such hydrophobic material is non-air-entraining when incorporated into cementitious materials (e.g., cement mortars and concretes). Preferably, hydrophobic material is an alkyl stearate ester, an alkyl oleate ester, or mixture thereof. More preferably, the hydrophobic material is butyl oleate (BO), butyl stearate (BS), or a mixture of these two, which may be used in a ratio (BO:BS) of 5:1 to 1:5; more preferably, in a ratio of 4:1 to 1:2; and, most preferably, in a ratio of 3:1 to 1:1.

Exemplary hydrophobic materials may also include fatty acids as well as their salts. For example, calcium stearate and zinc stearate may be used, and these are commercially available (both in powder form) from NORAC, Inc. Another example is tall oil fatty acid (TOFA) which is available from Grace Construction Chemicals, Cambridge, USA, under the tradename RX-901.

Exemplary hydrophobic materials may also include natural waxes, such as paraffinic wax, ceresin wax, and beeswax. Exemplary synthetic waxes may also be used. For example, such waxes are commercially available from Dow Chemicals under the tradename Carbowax®.

Exemplary hydrophobic materials may also include naturally occurring oils (e.g., coconut oil, castor oil), some of these being already noted above, as well as synthetic oils.

Other exemplary hydrophobic materials are silicones, silanes, and siloxanes. For example, butyltrimethoxysilane and other silanes are commercially available from Dow Corning. A wide range of organosilicon compounds are available as well from Dow Corning.

Still further exemplary hydrophobic materials believed to be suitable for purposes of the invention include naphthalene compounds (e.g., bis isoproponyl naphthalene, calcium di(naphthalene) sulfonate), and also melamine compounds.

Another exemplary hydrophobic material is a dicarboxylic acid or the salt thereof. Such materials will have the chemical formula

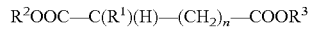

wherein $R^1$ is a $C_{12}$ to $C_{18}$ alkyl or alkylene group; $R^2$ and $R^3$ are hydrogen or a cation (e.g., sodium, potassium, lithium, zinc, butyl), and "n" is an integer from 1 to 6. A preferred dicarboxylic salt is di-sodium salt of tetrapropenyl butanediodic acid, having the formula

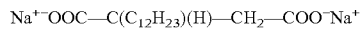

For example, a 20% solution of this dicarboxylic salt ("DSS") can be mixed into a glycol ether solvent as follows: 45% DPTB, 450% DPG, 2% DSS, and 8% water (wherein "DPTB" represents di(oxypropylene)glycol-t-butyl ether and "DPG" represents di(oxypropylene)glycol.

Exemplary glycol ether solvents believed to be suitable for use in the invention comprise (i) an oxyalkylene glycol; (ii) an oxyalkylene ether adduct of an alcohol, glycol, or glycerol; or (iii) a mixture thereof. Exemplary oxyalkylene glycols which are believed to be suitable for use in the present invention can be represented by the formula $HO(AO)_nH$ wherein: A represents a $C_2$-$C_4$ alkylene group (such as ethylene, propylene, butylenes, and the like, along with mixtures thereof, with ethylene and propylene being most preferred); O represents an oxygen atom, and n represents an integer of from 1 to about 30, and more preferably 1-3. The AO groups in a particular glycol molecule may be the same or may be different. Examples of such glycols include diethylene glycol, dipropylene glycol, tripropylene glycol, di(ethoxy)(di(propoxy) glycol and the like. Further glycols may include polyalkylene glycols (poly(oxyalkylene)glycols) having molecular weights up to about 1200. The AO groups forming the chain of such glycols may contain a single type of alkylene ether group or a mixture of alkylene ether groups which may be in block or random arrangement. Examples of the oxyalkylene glycols are polypropylene glycol, polyethylene glycol, poly (oxyethylene)(oxypropylene)glycol and the like.

Exemplary oxyalkylene adducts of monoalcohols which are believed to be suitable for use in the invention can be represented by the formula $RO(AO)_mH$ wherein R is a hydrocarbon group, such as a $C_1$-$C_7$ alkyl or a $C_5$-$C_6$ cycloalkyl group; A represents a $C_2$-$C_4$ alkylene group, O represents an oxygen atom and m represents an integer of from 1 to about 10. Examples of such R groups are methyl, ethyl, propyl, isopropyl, n-butyl, isobutyl, t-butyl, n-pentyl, isopentyl, cyclopentyl, cyclohexyl and the like. The preferred R groups are $C_3$-$C_5$ alkyl such as n-propyl, isopropyl, n-butyl, t-butyl and the like. In various embodiments of the invention, is preferred that the R groups be the same. A is a $C_2$-$C_4$ (preferably $C_2$-$C_3$) alkylene group, such as ethylene, propylene and the like and mixtures thereof in the same chain, and m is an integer of from 1 to about 10, preferably 2 or 3.

In preferred embodiments, the solvent is di(oxypropylene) glycol-tertiary-butyl ether ("DPTB"), di(oxypropylene)glycol-n-butyl ether ("DPNB"), or a mixture thereof, optionally with di(oxypropylene)glycol ("DPG"), di(oxyethylene)glycol (DEIG), or mixture thereof.

Exemplary compositions of the invention therefore comprise at least one hydrophobic material which could include a stearate, an oleate, a naturally occurring oil, a laurate, a palmitate, a myristic ester, a linoleic ester, or a salt thereof, or a mixture thereof; and a glycol ether solvent which could include (i) an oxyalkylene glycol; (ii) an oxyalkylene ether adduct of an alcohol, glycol, or glycerol; or (iii) a mixture thereof. In most preferred compositions, the at least one hydrophobic material comprises butyl oleate and butyl stearate, and the glycol ether solvent is DPTB, DPNB, or a mixture thereof, optionally with low molecular weight DPG or DIEG. These solvents are especially preferred because they have excellent shrinkage and air detraining capabilities when incorporated into hydratable cementitious mixtures. Hence, preferred solvents are operative to detrain air in cementitious materials.

Further exemplary compositions of the invention may comprise at least one comb polymer superplasticizer, as conventionally used in the industry, for improving plasticity, workability, and/or slump as may be desired. Most preferred are comb polymer superplasticizers having pendant poly(oxyalkylene) groups. Such plasticizers are generally known. A suitable superplasticizer is commercially available from Grace under the tradename ADVA®. Superplasticizers can be incorporated into compositions of the invention, preferably after the solute(s) and solvent are mixed thoroughly together, in an amount of 5 to 30 percent based on total weight of the composition. Poly(oxyalkylene) superplasticizers may contain a small amount of water as a result of formulation or manufacture. However, it is preferable that the total amount of water not exceed 30% by total volume of composition, and more preferably not exceed 5% by total volume of composition.

carboxylic acid, into glycol ether. These resulted in transparent solutions as confirmed by shining a laser through the liquid. (According to Tyndall, a solution will not scatter the laser beam, whereas an emulsion or dispersion will). Unlike emulsions, these solutions are stable at a high temperature of 46 degrees C. and will revert to a solution if taken below solidification temperature and melted. In addition, viscosities at low temperatures are well below the 250 cP criterion needed for pumping with standard admixture pumps. The data is presented in Table 1 below. Sample 1 shows the benefit of using DPNB and DPG to reduce the freezing point of butyl oleate ("BO") and butyl stearate ("BS") blends.

TABLE 1

| | % Components | | | | At 2° C. | | 5° C. | | 46° C. |
|---|---|---|---|---|---|---|---|---|---|
| Sample | DPNB | DPG | BO | BS | Form | Viscosity (cP) | Form | Viscosity (cP) | Form |
| 1 | 38 | 21 | 20.5 | 20.5 | HS* | — | HL** | 21 | HL |
| 2 | 38 | 21 | 27.3 | 13.7 | HL | 23.8 | HL | 20.1 | HL |
| 3 | 38 | 21 | 30.75 | 10.25 | HL | 23.7 | HL | 20.5 | HL |
| 4 | 0 | 0 | 67 | 33 | HS | | | | HL |
| 5 | 29.5 | 29.5 | 20.5 | 20.5 | HS | | HL | | HL |
| 6 | 29.5 | 29.5 | 27.3 | 27.7 | HL | | HL | | HL |
| 7 | 33 | 33 | 17 | 17 | HL | | HL | | HL |
| 8 | 33 | 33 | 22.7 | 11.3 | HL | | HL | | HL |

*HS = Homogeneous solid/gel;
**HL = Homogeneous liquid solution;
DPNB = dipropylene glycol n butyl ether;
DPG = dipropylene glycol
BO = butyl oleate;
BS = butyl stearate Preferably, the compositions of the invention are substantially devoid of surfactants, or other surface active agents, as would normally be otherwise required to form emulsion systems. Thus, the use of a metal salt (e.g., sodium, potassium, lithium) of a fatty acid or tall oil fatty acid is less preferred due to the tendency of such metal salts to entrain air when incorporated into cementitious materials; and thus, if certain metal salts are used as hydrophobic materials, it may be advisable to employ an air-detraining agent.

Exemplary methods of the invention therefore include modifying a cementitious material by introducing to a hydratable cementitious material the above-described water repellency enhancing compositions. As previously mentioned, these can be incorporated as additives during the manufacture of cement from clinker, or as admixtures incorporated into the finished cement, mortar, concrete, or other cementitious mixture.

The following examples are provided for illustrative purposes.

EXAMPLE 1

Several solutions of the invention were produced by dissolving an organic ester of an aliphatic acid, or an aliphatic

EXAMPLE 2

An exemplary additive of the invention, wherein a hydrophobic material was dissolved in a glycol ether shrinkage reducing solvent to obtain the additive, was shown to enhance moisture impermeability of concrete samples. This enhanced impermeability was confirmed in terms of reducing water absorption, shrinkage, and electrical conductivity, in comparison to concrete samples not containing the additive.

The improvements are seen in concretes having high water-to-cement ratios (w/c) as well as lower w/c ratios which are typical of less permeable concretes. Table 2 shows typical improvements in the British Absorption Test (BS 1881 Part 122) for composition 1, 2 and 3 from Table 1 denoted as "IWC1," "IWC2," and "IWC3." This is a key test for evaluating admixtures for achieving integral waterproofing of cementitious compositions, and numbers of about 1% or less are considered excellent.

The data suggests that IWC mixes had better workability with lower superplasticizer levels than shrinkage reducing admixture (SRA) used alone (Mixture 10), and had reduced absorption levels when compared to SRA used alone, and showed a 25% improvement at two-thirds dosage.

TABLE 2

| Mixture | Polycarboxylate Superplasticizer (oz/cwt)* | Air (%) | Final Slump (in)** | UW (pcf) | British Absorption % |
|---|---|---|---|---|---|
| 1. Control 0.5w/c | 2.5 | 4 | 8.00 | 151.7 | 2.8515 |
| 2. Control 0.4w/c | 6 | 2.4 | 7.00 | 151.7 | 1.8487 |
| 3. WC1/@.5gpy | 6 | 1.7 | 7.50 | 158.9 | 0.9925 |

TABLE 2-continued

| Mixture | Polycarboxylate Superplasticizer (oz/cwt)* | Air (%) | Final Slump (in)** | UW (pcf) | British Absorption % |
|---|---|---|---|---|---|
| 4. IWC1/@.075gpy | 6 | 1.7 | 7.25 | 158.5 | 0.9819 |
| 5. IWC1/@1gpy | 5.5 | 1.8 | 4.00 | 157.8 | 0.9266 |
| 6. IWC2/@0.5gpy | 6 | 1.4 | 7.25 | 159.0 | 1.0174 |
| 7. IWC3/@0.5gpy | 6 | 1.5 | 7.25 | 158.5 | 0.9439 |
| 8. IWC2/@0.75gpy | 8 | 1.7 | 7.50 | 158.1 | 0.9338 |
| 9. IWC3/0@0.75gpy | 6.5 | 1.7 | 6.50 | 158.2 | 0.9715 |
| 10. 50% DPNB/ 50% DPG@0.75gpy | 12 | 2.4 | 4.00 | 156.4 | 1.2618 |

*The polycarboxylate Superplasticizer was Grace Construction Products brand available under the tradename Adva ®.
**Slump is an indication of workability and is measured using the standard slump cone technique, and values shown were found to be between 4 and 8 inches which is desirable for normal concretes used in flooring and wall applications.

EXAMPLE 3

Properties for various mixes produced using IWC1, SRA, and damp-proofing materials such as calcium stearate emulsion (Grace Darapel® brand), butyl oleate, and butyl stearate. The damp-proofing materials have a minor effect on drying shrinkage. As shown in Example 2 above, the SRA does not reduce water absorption as well as the IWC samples.

Synergy was surprisingly discovered by dissolving the hydrophobic material or materials in a shrinkage reducing admixture (SRA) solvent before addition to cement or concrete, because the combined additive allowed for lower overall component dosages in comparison to separate use of hydrophobic material and separate use of the SRA.

Furthermore, less air was created in the concrete than was the case with separately added damp-proofing components. This is beneficial for interior flooring applications.

Permeability of concrete samples was measured using methodology similar to that described in ASTM C 1202. Current across the ends of a cylindrically shaped concrete sample having a 4-inch diameter by 12-inch length was measured at 60 Volts DC after one minute. Higher currents correspond to concretes having higher permeability to water and moisture. It is noted that reducing the water/cement ratio of the concrete from 0.5 to 0.4 had a major effect, and the addition of calcium stearate by itself showed little improvement. However, the concrete mixtures having the IWC additives of the invention showed a significant drop. It was found that although the hydrophobic material or the shrinkage reducing admixtures (SRA), when used separately, could match or exceed some of the qualities of the IWC samples of the invention, the IWC samples used less overall material and achieved favorable reductions in absorption, permeability, and shrinkage all across the board.

EXAMPLE 4

Other hydrophobic solute materials that can provide excellent properties are naphthalenes, e.g., Ruetasolv DI, which is $C_{16}H_{20}$, Naphthalene, bis(1-methylethyl)-(9Cl). When added at 1:2 to 2:1 to 50% dipropylene glycol t-butyl ether/50% dipropylene glycol, the naphthalene formed a clear solution as confirmed by laser light test, and was also found to be soluble in IWC2 (See Formula 2 in Table 1). Properties of concrete samples made using these materials, compared to control samples, are shown in Table 4. Reducing the water-to-cement (w/c) ratio slightly improved initial capillary absorption (Si) as measured using ASTM C 1585. However, there was a significant reduction in Si when additives of the invention were employed, as well as a significant decrease in shrinkage (in comparison to samples wherein w/c ratio was merely lowered).

TABLE 4

| Formulation | w/c | Si (mm-s$^{-1/2}$) | 28-day shrinkage after 7 days moist curing (%) | Current (mA) (Modified ASTM C1202) at 28 days wet curing |
|---|---|---|---|---|
| 1. Control 1 | 0.5 | 30.5 | 0.0335 | 55.6 |
| 2. Control 2 | 0.4 | 26.5 | 0.0245 | 33.9 |
| 3. 25% DPTB/ 25% DPG/ 50% Ruetasolv | 0.4 | 10.5 | 0.0075 | 34.3 |
| 4. 66.7% DPNB/ 33.3% RUETASOLV | 0.4 | 10.0 | 0.0145 | 31.6 |

TABLE 3

| Mix # | Mixture | BSI Abs. | ASTM C157 Drying Shrinkage 28 days drying 1-day cure in mold | Air (%) | Current (mA) (Modified ASTM C1202) at 12 days wet curing |
|---|---|---|---|---|---|
| 04353-1 | Control 0.5w/c | 2.83 | 0.0675 | 2.5 | 69.2 |
| 04353-2 | Control 0.4w/c | 1.84 | | 2.4 | 45.3 |
| 04353-3 | Control 0.4w/c 1.0 galDarapel | 0.96 | 0.0465 | 2.7 | 43.6 |
| 04353-4 | Control 0.4w/c 1.5 galDarapel | 0.73 | 0.0535 | 2.9 | 44.1 |
| 04353-5 | IWC1@.5gpy | 1.08 | 0.042 | 1.9 | 37.245 |
| 04353-6 | IWC1@.75gpy | 0.98 | 0.040 | 1.5 | 37.455 |
| 04353-7 | IWC1@1gpy | 0.90 | 0.036 | 1.5 | 34.68 |
| 04353-8 | DPNB/DPG50/50)@1gpy | 1.20 | 0.0315 | 1.9 | 38.94 |
| 04353-9 | 50/50BO/BS@0.5gpy | 0.82 | 0.0515 | 1.7 | 37.535 |

EXAMPLE 5

Stable non-oil-in-water emulsions were made using glycol ether to provide a continuous liquid phase and a naphthalenesulfonic acid as the hydrophobic material. An exemplary hydrophobic material was NaCorr® which is a tradename for naphthalenesulfonic acid, dinonyl-calcium salt ($C_{28}H_{44}O_3S.1/2Ca$)). This additive, when employed in a concrete sample, provided benefits in terms of reducing shrinkage and absorption. Laser light tests confirmed that these formulations are emulsions in at least a range of 1:2 to 2:1 mass ratio to the glycol ether. They did not freeze or separate at temperatures from −5 to +46 degrees Celcius. Shrinkage and absorption data of samples containing the hydrophobic agent in a glycol ether shrinkage reduction agent (SRA), using an SRA available from Grace Construction Products under the tradename ECLIPSE® are summarized in the table below.

TABLE 5

| Formulation | Shrinkage at 28 days (7-day wet cure) % | Capillary Absorption* $C_{ab}$ (g/m²-s$^{1/2}$) |
|---|---|---|
| 1. Control | 0.029 | 13.3 |
| 2. Eclipse (1.5 gpy) | 0.014 | 10.8 |
| 3. 25% DPTB/25% DPG/50% NaCorr | 0.0165 | 8.93 |

Note all concrete at 0.45 w/c.
*3-inch × 3-inch cylinders dried at 70° C., cooled to 21° C., and placed in water at 21° C.

EXAMPLE 6

A wide range of formulations of the invention was tested to demonstrate that formed stable solutions or non-oil-in-water emulsions could be provided. The combinations, which are provided for illustrative purposes only and are not inclusive of all potential combinations realizable from the present disclosure, are identified in Table 6 below.

TABLE 6

| Formula | DPNB | DPG | BO | BS | DPTB | Ruetasolv | NaCorr | Stearic Acid | Stable Solution (S) or Emulsion (E) |
|---|---|---|---|---|---|---|---|---|---|
| 1 |  | 33.3 |  |  | 33.3 |  | 33.4 |  | E |
| 2 |  | 16.7 |  |  | 16.7 |  | 66.6 |  | E |
| 3 |  | 25 |  |  | 25 |  | 50 |  | E |
| 4 |  | 16.7 |  |  | 16.7 |  | 66.6 |  | S |
| 5 |  | 25 |  |  | 25 |  | 50 |  | S |
| 6 |  | 33.3 |  |  | 33.3 |  | 33.4 |  | S |
| 7 | 66.6 |  | 16.7 | 16.7 |  |  |  |  | S |
| 8 | 66.7 |  | 30 | 3.3 |  |  |  |  | S |
| 9 | 38 | 21 | 20.5 | 20.5 |  |  |  |  | S |
| 10 | 38 | 21 | 27.3 | 13.7 |  |  |  |  | S |
| 11 | 38 | 21 | 30.75 | 10.25 |  |  |  |  | S |
| 12 | 38 | 21 | 41 | 0 |  |  |  |  | S |
| 13 | 34.2 | 18.9 | 24.6 | 12.3 |  | 10 |  |  | S |
| 14 | 34.2 | 18.9 | 24.6 | 12.3 |  |  | 10 |  | S |
| 15 | 34.2 | 18.9 | 18.45 | 18.45 |  |  | 10 |  | S |
| 16 |  | 46.75 |  |  | 46.75 |  |  | 6.5 | S |
| 17 | 47.5 |  | 23.75 | 23.75 |  |  |  | 5 | S |

EXAMPLE 7

Further exemplary hydrophobic materials were into DPTB and DPG. These hydrophobic materials included tall oil fatty acid (TOFA), a metal salt of a fatty acid (e.g., zinc stearate), and a wax (e.g., polyethylene glycol, about 200 molecular weight, available from Dow Chemical as CARBOWAX). TOFA (50%) was blended with DPTB (25%) and DPG (25%) formed a stable mixture at room temperature, percentages based on weight). Zinc stearate (5.6%) was blended with DPTB (47.2%) and DPG (47.2%) and also provided a stable mixture at room temperature. The wax (33.4%) was blended with DPTB and DPG each at 33.3%, and provided a stable mixture at room temperature.

EXAMPLE 8

A further exemplary stable solution of the invention was made by combining a hydrophobic material, polyethylene glycol (PEG) having approximately 1000 molecular weight, in di(oxypropylene)glycol-t-butyl ether (DPTB) and di(oxypropylene)glycol (DPG), in the following ratio: 47.15% DPTP, 47.15% DPG, and 5.7% PEG. The PEG was commercially available from DOW under the tradename CARBOWAX 1000.

EXAMPLE 9

A still further exemplary stable solution of the invention was made by dissolving a 20% solution of di-sodium salt of tetrapropenyl butandediodic acid, having the formula $Na^+$ $OOC-C(C_{12}H_{23})(H)-CH_2-COO^-Na^+$ into DPTB and DPG, such that the final solution had the following components: 45% DPTB, 45% DPG, 2% DSS, and 8% $H_2O$. Another solution was made and also found to be stable, and this had the following components: 35% DPTB, 35% DPG, 6% DSS, and 24% $H_2O$. It is believed that increasing the amount of the hydrophobic material, without using the aqueous solution (so that no water would be introduced into the solution), would also work.

EXAMPLE 10

A still further exemplary stable solution of the invention was made by incorporating a silane (e.g., i-butyltrimethoxysilane from Dow Corning under the tradename Z-2306) in solvent, as follows: 29.4% DPTB, 29.4% DPG, and 41.2% Z-2306. This rendered a clear solution at room temperature The foregoing examples and exemplary embodiments are provided for illustrative purposes and are not intended to limit the scope of the invention.

It is claimed:

1. A liquid admixture composition for enhancing water repellency in a cementitious material, comprising:

a solute portion of said liquid admixture composition having at least one hydrophobic material selected from butyl stearate, butyl oleate, or mixture thereof, which is operative to enhance water repellency in cementitious material; and a non-aqueous solvent portion of said liquid admixture composition having at least one glycol ether selected from the group consisting of di(oxypropylene)glycol-t-butyl ether, di(oxypropylene)glycol-n-butyl ether, or mixture thereof, which non-aqueous solvent portion inhibits drying shrinkage in cementitious material;

said solute and solvent portions being present in said liquid admixture composition in a ratio of 95:5 to 5:95; said solute and solvent portions being mixed uniformly together by dissolving said at least one hydrophobic material in said solvent before combining with a hydratable cementitious material, said solute and solvent portions of said liquid admixture composition thereby forming a non-aqueous solution or an emulsion wherein water, if present, is present as a non-continuous phase;

said uniformly-mixed-together solute/solvent liquid admixture composition being effective, when combined with a hydratable cementitious material, to provide water repellency in a structure formed when the hydratable cementitious binder is combined with water and allowed to harden; and said liquid admixture composition comprising water in an amount of 0%-5% based on total weight of said liquid admixture composition.

2. The composition of claim 1 wherein said composition is devoid of water.

3. The composition of claim 1 wherein, in said composition, said solute and said solvent are present in a ratio of 70:30 to 30:70.

4. The composition of claim 1 wherein, in said composition, said solute comprises a butyl oleate and a butyl stearate.

5. The composition of claim 4 wherein, in said composition, said butyl oleate and butyl stearate are present in an amount no less than 30 percent and in an amount no greater than 50 percent based on dry weight total solids in said composition.

6. The composition of claim 1 further comprising di(oxypropylene)glycol, di(oxyethylene)glycol, or mixture thereof.

7. The composition of claim 1 wherein, in said composition, said at least one solvent is operative to detrain air.

8. The composition of claim 1 wherein said composition further comprises at least one comb polymer superplasticizer.

9. The composition of claim 1 further comprising at least one comb polymer superplasticizer having poly(oxyalkylene) groups.

10. The composition of claim 1 wherein said composition is in the form of a non-aqueous solution.

* * * * *